United States Patent [19]

Green

[11] 4,152,920
[45] May 8, 1979

[54] SYSTEM FOR APPLYING SURGICAL CLIPS

[75] Inventor: David T. Green, Norwalk, Conn.

[73] Assignee: United States Surgical Corporation, Stamford, Conn.

[21] Appl. No.: 843,063

[22] Filed: Oct. 17, 1977

[51] Int. Cl.² .................... B21D 9/08; A61B 17/10
[52] U.S. Cl. .................... 72/410; 29/243.56; 128/325
[58] Field of Search ............ 72/409, 410; 128/325, 128/334 R, 335, 346; 29/243.56; 227/19

[56] References Cited

U.S. PATENT DOCUMENTS

| 2,968,041 | 1/1961 | Skold | 128/335 |
| 3,777,355 | 12/1973 | Cooke | 29/243.56 |
| 3,777,538 | 12/1973 | Weatherly | 128/325 |
| 3,856,016 | 12/1974 | Davis | 128/325 |
| 3,924,629 | 12/1975 | Akiyama | 128/325 |

FOREIGN PATENT DOCUMENTS 1452185  10/1976  United Kingdom ............ 128/325

Primary Examiner—C. W. Lanham
Assistant Examiner—Gene P. Crosby
Attorney, Agent, or Firm—Fleit & Jacobson

[57] ABSTRACT

Novel system for applying surgical clips consisting of an instrument and disposable cartridge that together create a forceps with the cartridge being quickly detachable from the instrument to permit easy and fast replacement during a surgical procedure. The instrument has ring handles as a forceps and they operate to reciprocate a driver. The cartridge includes clinching jaws and a clip magazine with the jaws quick detachably connected to the instrument in a fixed manner whereas an actuator for the jaws is quick detachably fixed to the reciprocal driver of the instrument. A number of surgical clips can quickly and successively be supplied to the clinching jaws of the cartridge.

27 Claims, 52 Drawing Figures

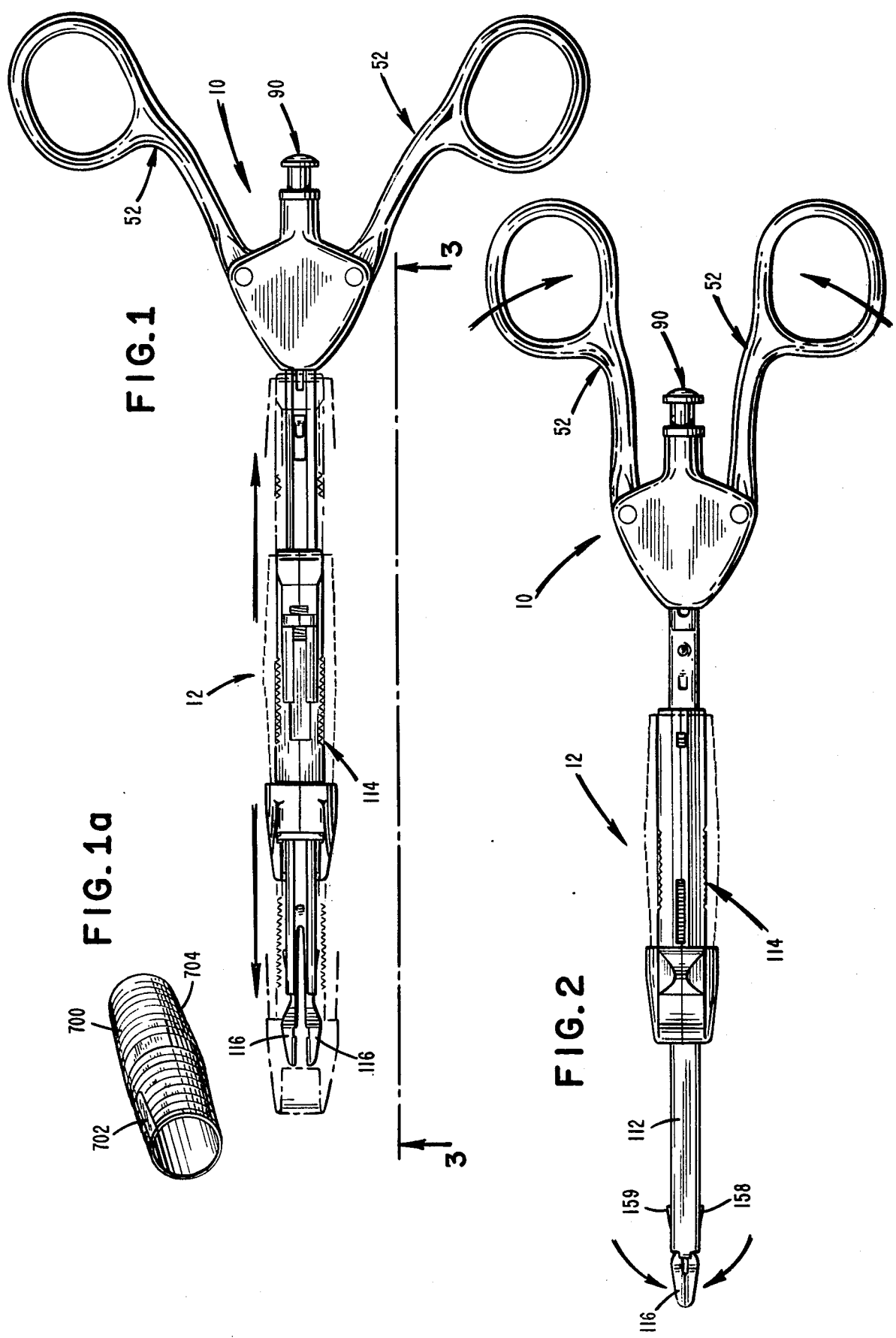

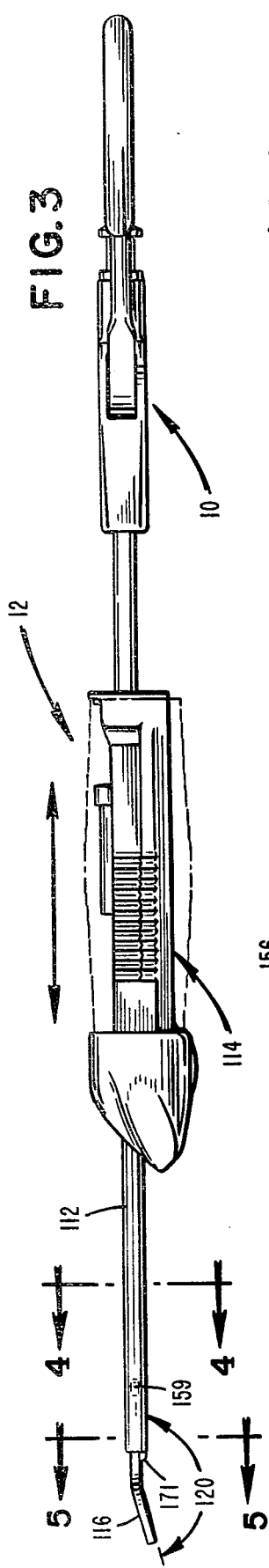
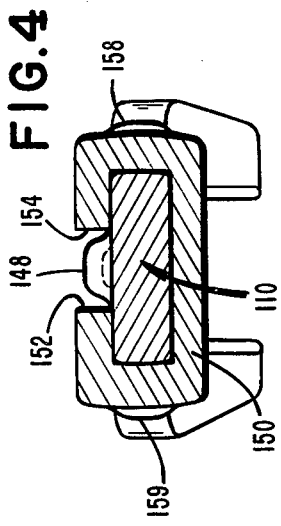
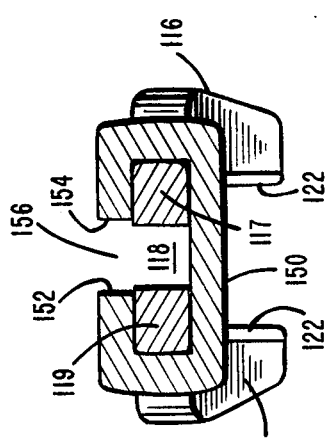
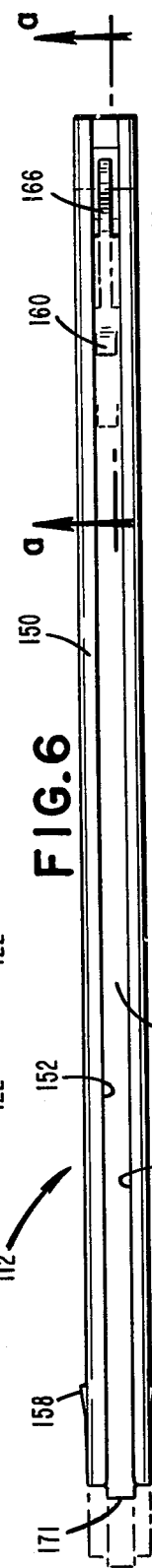
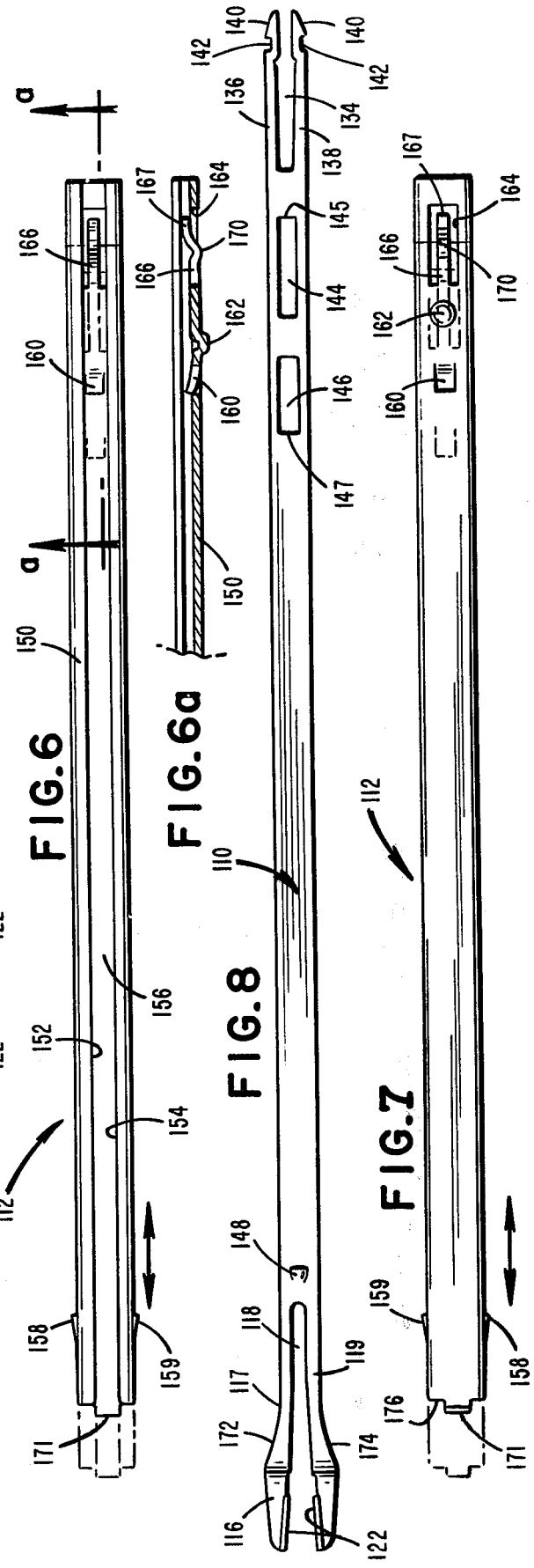

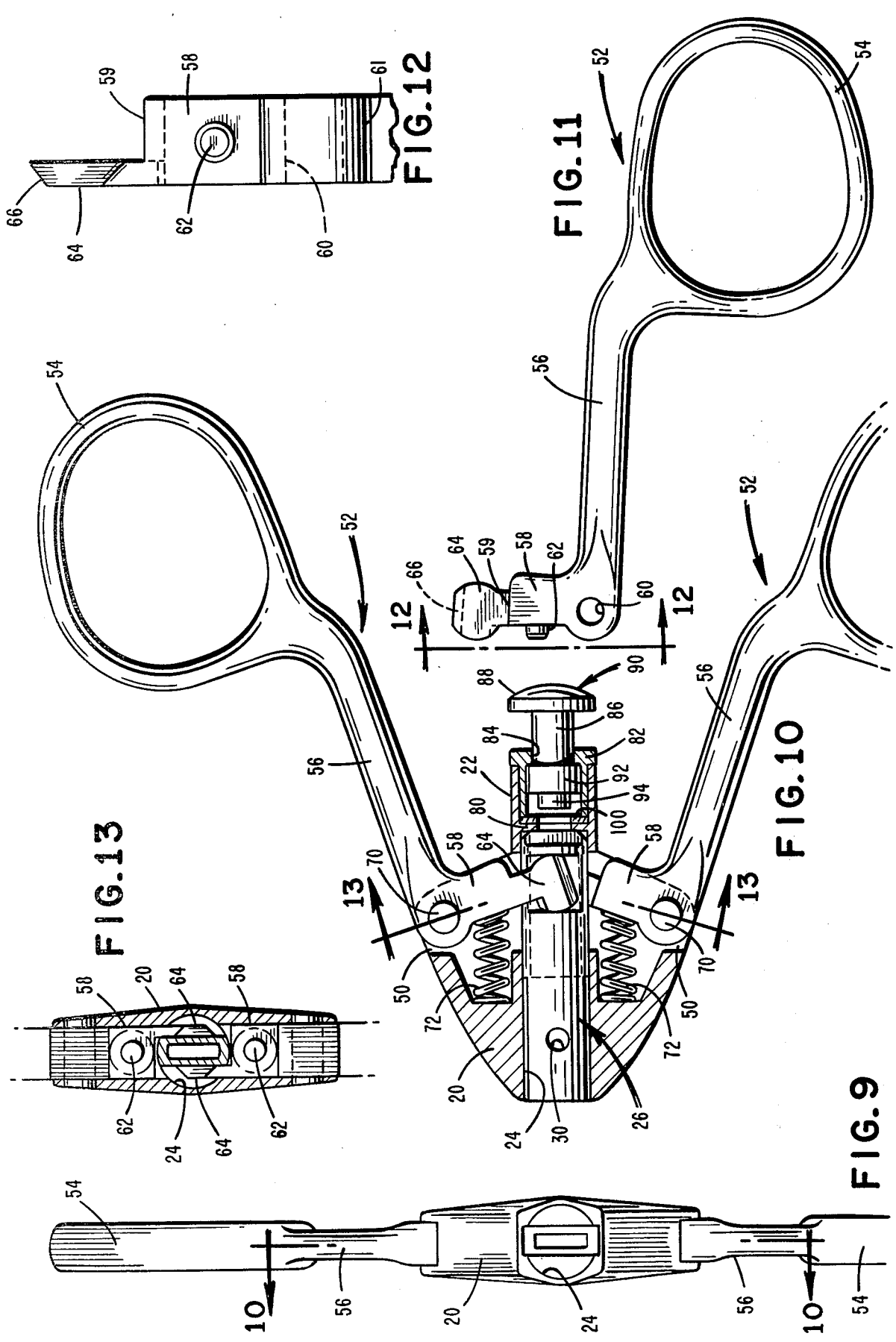

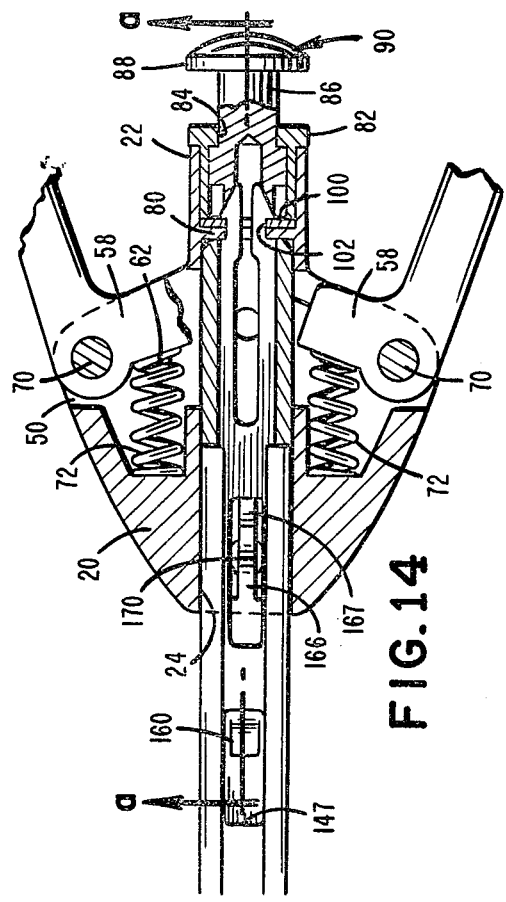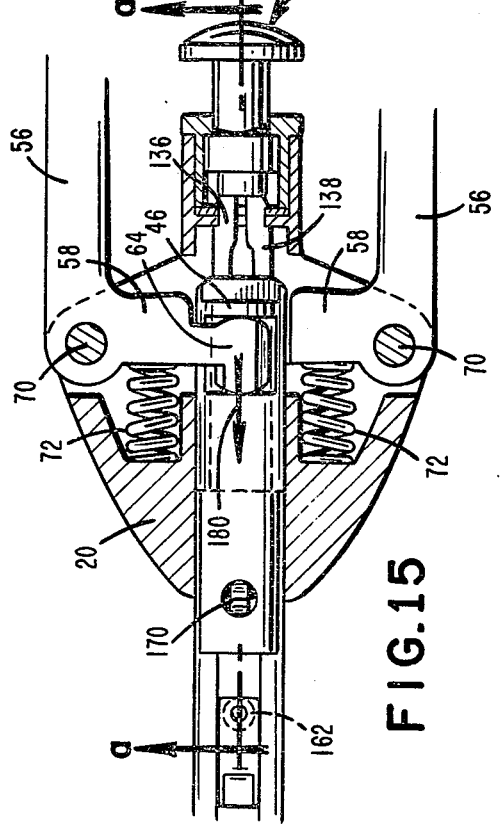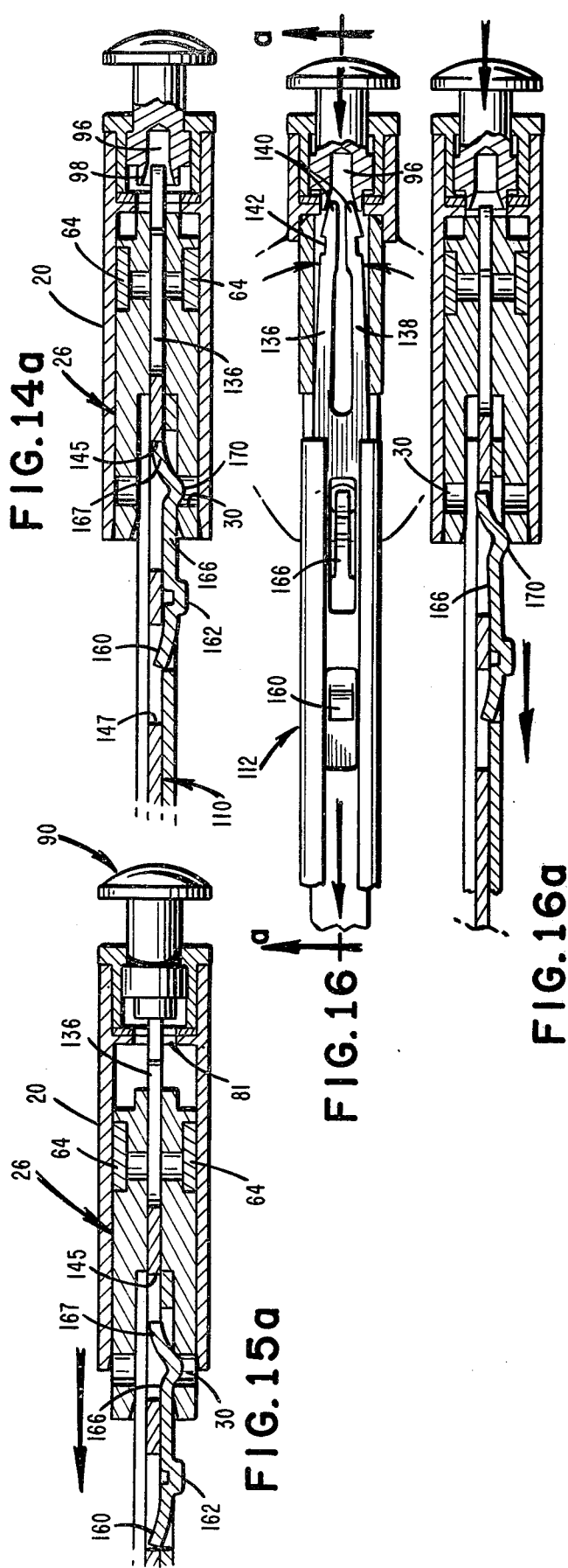

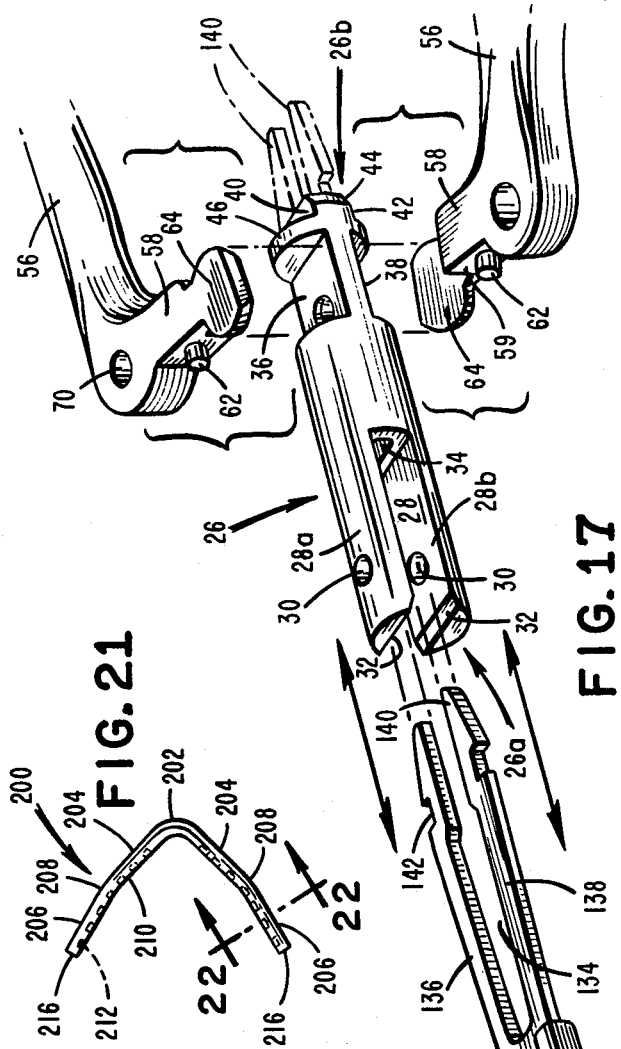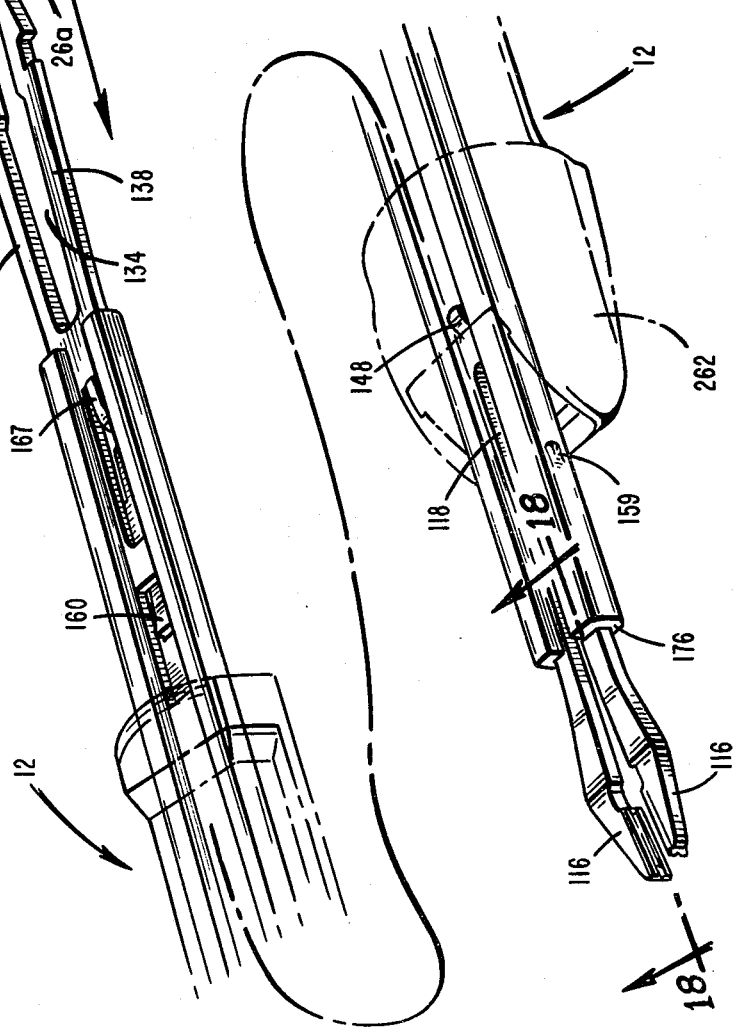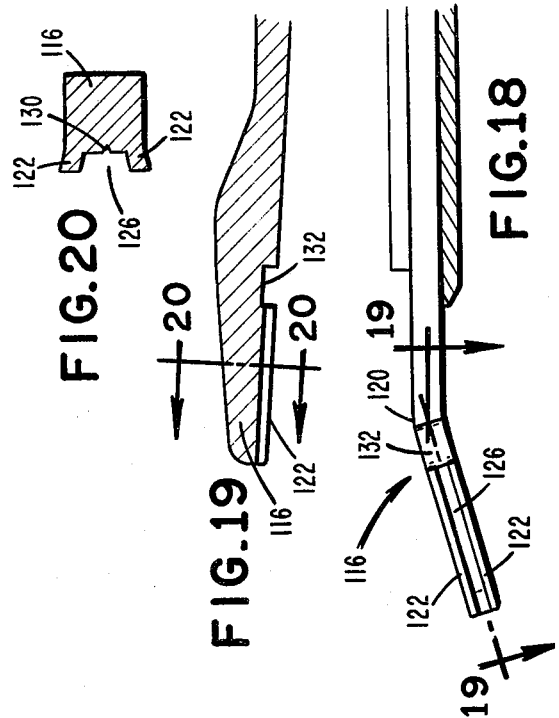

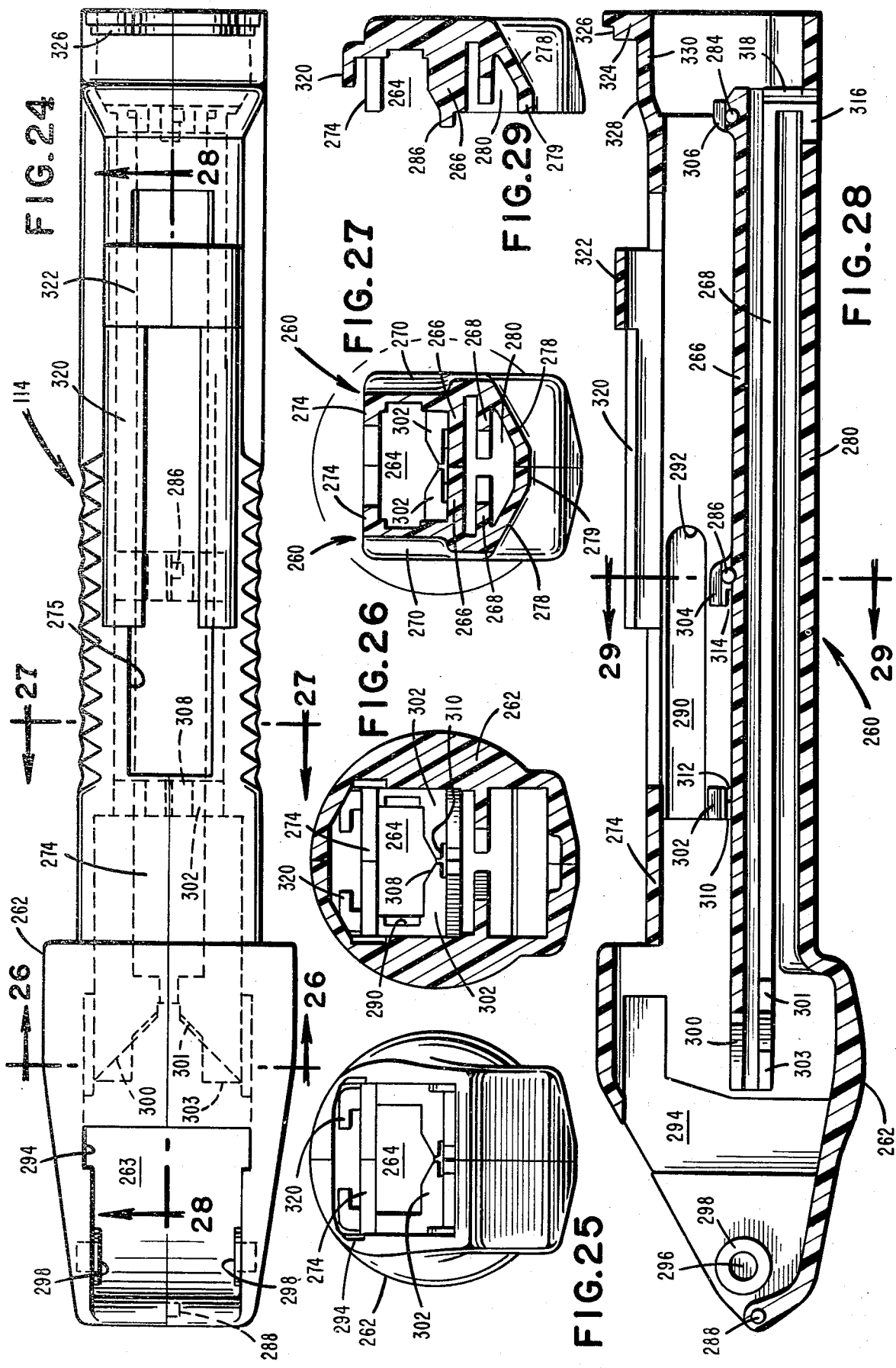

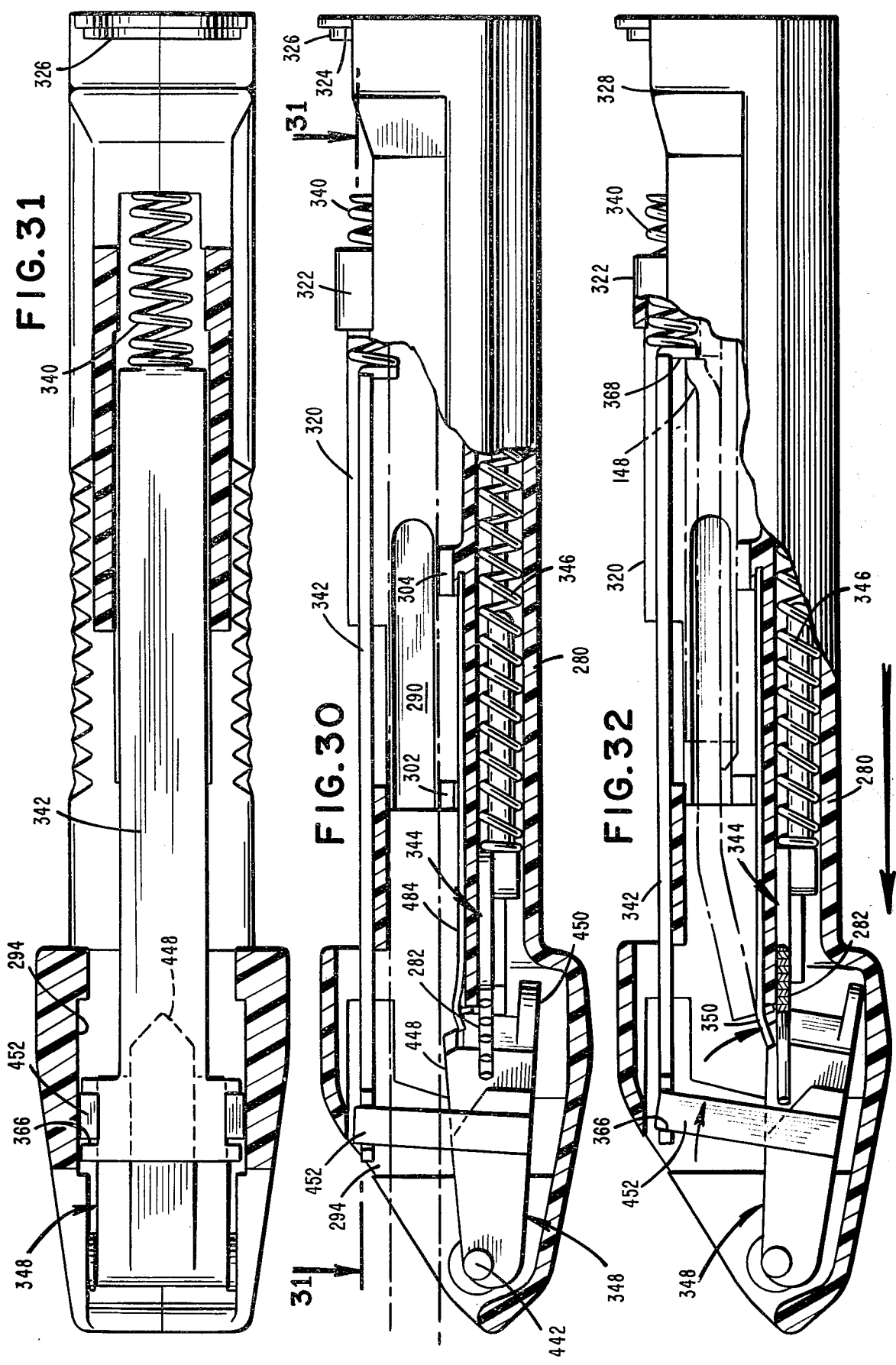

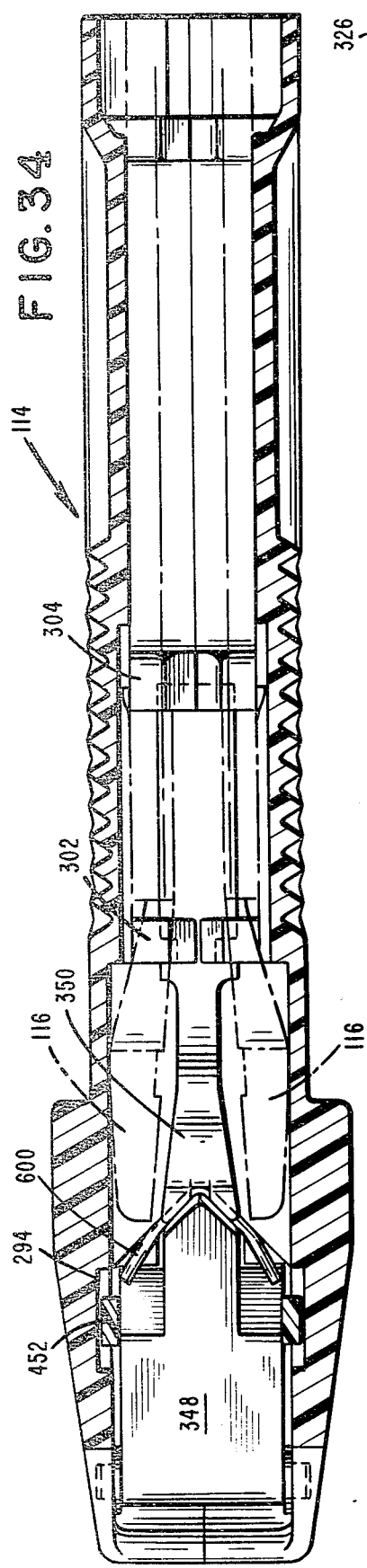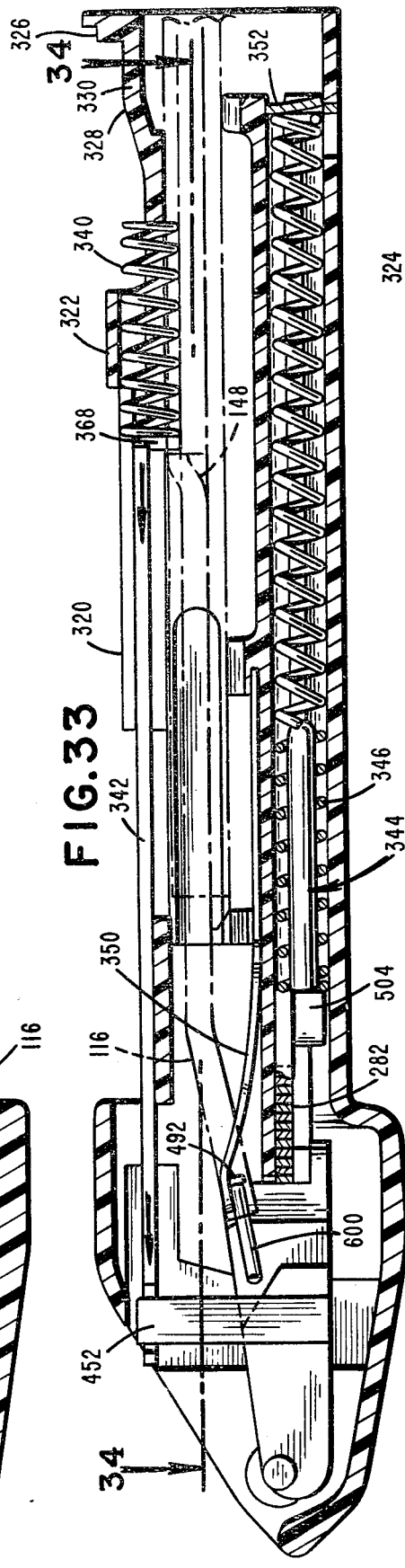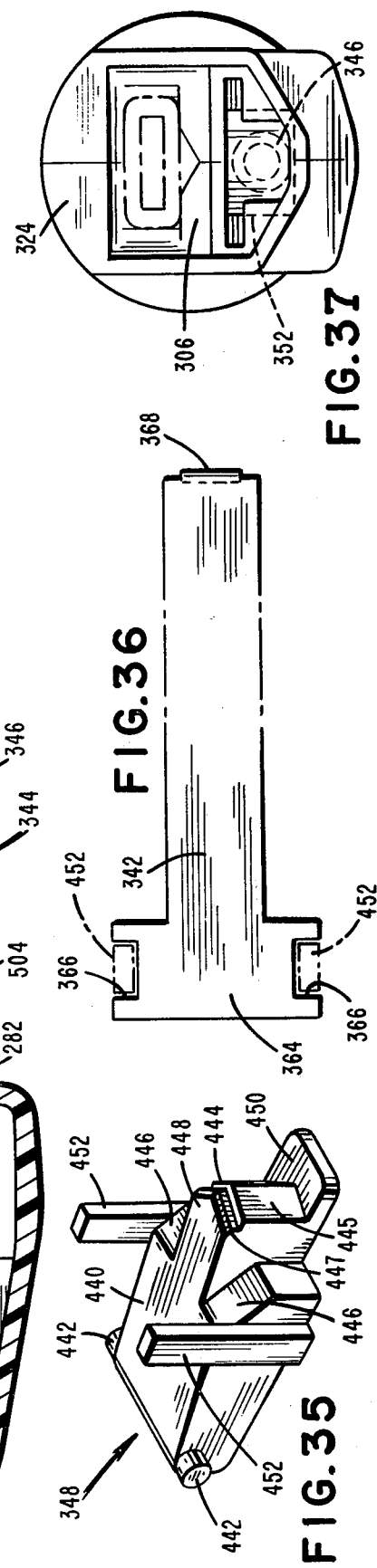

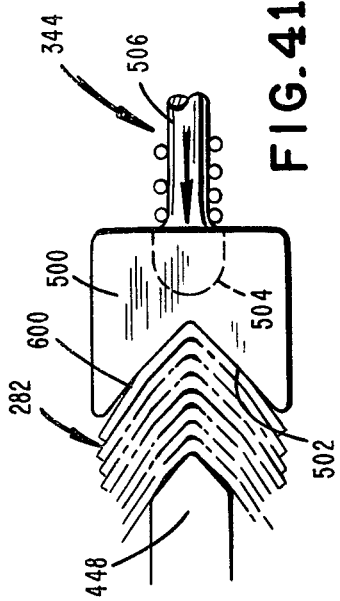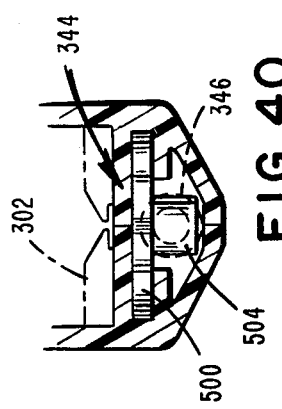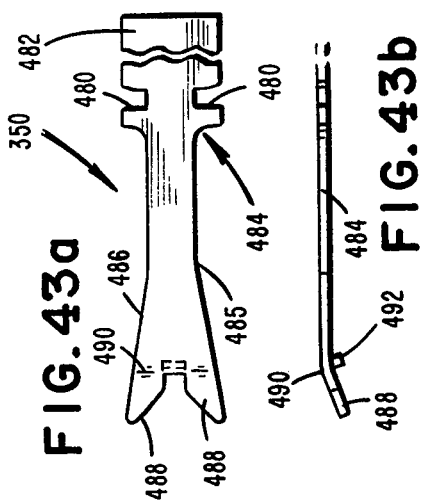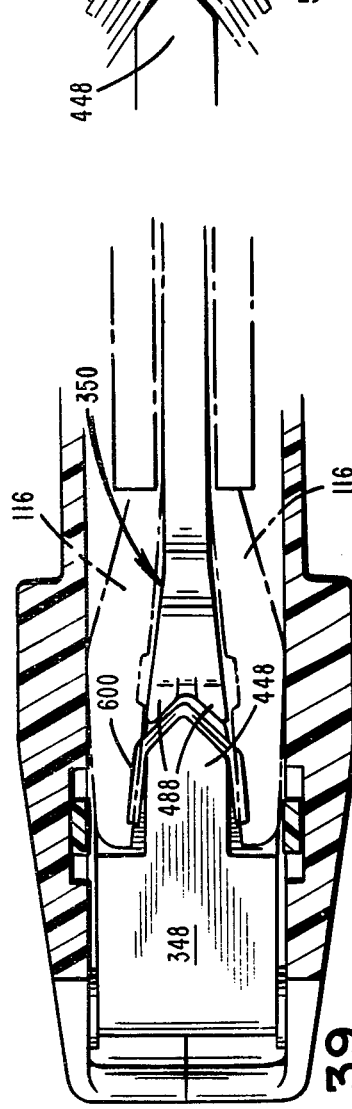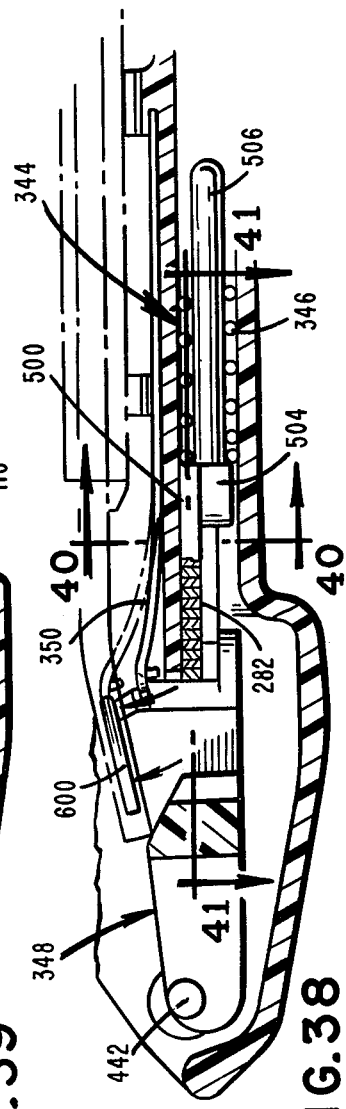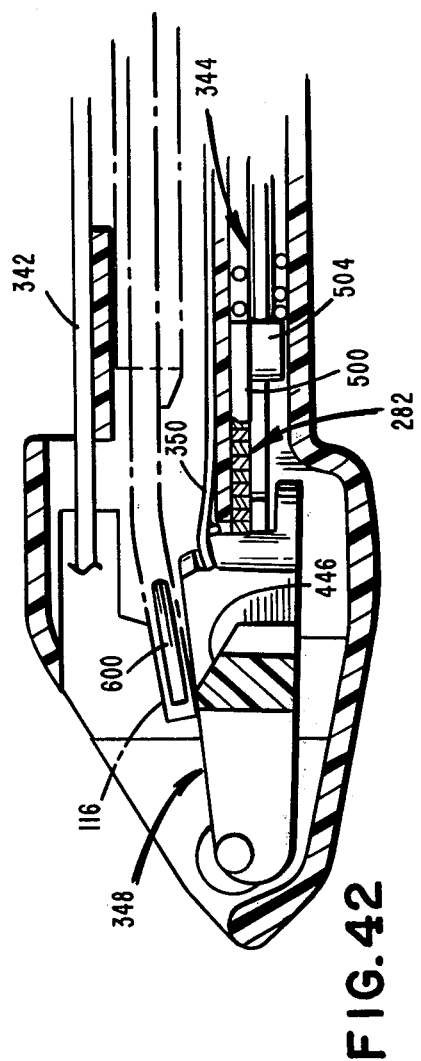

SYSTEM FOR APPLYING SURGICAL CLIPS

BACKGROUND OF THE INVENTION

The present invention relates to a novel system for applying for surgical clamps or clips which incorporates a novel disposable cartridge assembly detachably mounted on an instrument.

Applicators for applying surgical clips or clamps which utilize or include a cartridge are known in the art, see for example U.S. Pat. Nos. 3,777,538; 3,232,089; and 2,968,041. The advantages of applicators of this type are enumerated at length in the specifications of the three patents noted above. The prior art, however, does not suggest a system for applying surgical clips which incorporates a disposable cartridge detachably mounted on an instrument in the unique manner of the present invention.

SUMMARY OF THE INVENTION

The principal object of the present invention is to provide a novel system for quickly and successively applying surgical clips or clamps which incorporates a novel disposable cartridge assembly, the system being more versatile and more useful than appliances of this type heretofore known. The invention also teaches a design concept by which the disposable cartridge is quick detachably attached to the instrument without the necessity for special orientation and accordingly, a surgeon, during an operating procedure, may quickly detach a used cartridge, grasp another disposable cartridge and quickly detachably connect same to the instrument without fear of misplacement or jamming. Further, the system includes a means on the cartridge assembly whereby the surgeon, either when mounting a cartridge or actuating a cartridge, may grasp same without imposing any torque or torsion on the cartridge or instrument thereby facilitating insertion as well as actuation of the disposable cartridge. The quick detachable disposable cartridge is comprised of a clip carrying housing which slides on a jaw blade and sleeve assembly thereby allowing the clip carrying housing to be retracted from the jaws of the disposable cartridge to enable placement of the jaws into small openings or spaces. These are only some features of the invention; others will become evident from the ensuing detailed description of the preferred embodiment.

Although the present invention is illustrated and described in terms of a specific preferred embodiment, nevertheless, it should be understood that specificity is only the means to demonstrate the generic concepts of the invention. No attempt is made in this specification to describe every generic concept by words or phrases but rather they may readily be induced from the specifics. These generic concepts are framed and drafted in the claims appended to the end of this specification.

BRIEF DESCRIPTION OF THE DRAWINGS

FIG. 1 is a view in top plan showing the novel system of the present invention for applying surgical clips and comprises a disposable cartridge detachably mounted on an instrument;

FIG. 1a is a view in perspective of the sleeve and lens assembly which is mounted on the exterior of the cartridge housing and which is shown in phantom in FIGS. 1, 2 and 3;

FIG. 2 is a view similar to FIG. 1 showing the instrument with its ring handles closed together and the cartridge with its clinching jaws closed together;

FIG. 3 is a side view of the instrument and cartridge of FIG. 1;

FIG. 4 is a view in section of FIG. 3 taken along lines 4—4;

FIG. 5 is a view in section of FIG. 3 taken along line 5—5;

FIG. 6 is a view in top plan of the wrap or sleeve component of the disposable cartridge;

FIG. 6a is a view in section of FIG. 6 taken along lines a—a;

FIG. 7 is a view in bottom plan of the sleeve illustrated in FIG. 6;

FIG. 8 is a view in top plan of the jaw blade component of the disposable cartridge assembly;

FIG. 9 is an end view of the instrument;

FIG. 10 is a view in section of FIG. 9 taken along line 10—10;

FIG. 11 is a view in plan of a ring handle component of the instrument;

FIG. 12 is an end view of the ring handle component illustrated in FIG. 11 taken along line 12—12;

FIG. 13 is a view in section of FIG. 10 taken along lines 13—13;

FIG. 14 is a view in horizontal section through the mid-plane of the instrument illustrating the detachable mounting of the disposable cartridge with the instrument;

FIG. 14a is a view in section of FIG. 14 taken along line a—a;

FIG. 15 is a view similar to FIG. 14 showing the action when the ring handles have been closed together;

FIG. 15a is a view in section of FIG. 15 taken along line a—a;

FIG. 16 is a view similar to FIGS. 14 and 15 illustrating detachment of the disposable cartridge from the instrument;

FIG. 16a is a view of FIG. 16 taken along line a—a;

FIG. 17 is an exploded view in perspective showing the interrelationship between the ring handles and the actuator rod of the instrument and the jaw blade and the sleeve of the disposable cartridge;

FIG. 18 is a side view partly in section illustrating the end of a jaw blade;

FIG. 19 is a view in section of FIG. 18 taken along line 19—19;

FIG. 20 is a view in section of FIG. 19 taken along line 20—20;

FIG. 21 is a side view of a novel surgical clip according to the present invention;

FIG. 22 is a view in section of FIG. 21 taken along line 22—22;

FIG. 23 is a side view of the novel surgical clip showing the same in a clinched or clamped state;

FIG. 24 is a view in top plan of the cartridge housing;

FIG. 25 is a view in end elevation of the cartridge housing looking into the nose of the cartridge;

FIG. 26 is a view in section of FIG. 24 taken along line 26—26;

FIG. 27 is a view in section of FIG. 24 taken along lines 27—27;

FIG. 28 is a view in section of FIG. 24 taken along lines 28—28;

FIG. 29 is a view in section of FIG. 28 taken along line 29—29;

FIG. 30 is a view in side elevation of a cartridge assembly partly broken away showing the clip magazine and advancing mechanism;

FIG. 31 is a view in section of FIG. 30 taken along line 31—31;

FIG. 32 is a view similar to FIG. 30 showing the anvil depressed;

FIG. 33 is a view in vertical section taken along the longitudinal mid-line of the cartridge assembly showing a clip in position on the anvil ready to be picked up by the jaws;

FIG. 34 is a view in section of FIG. 33 taken along line 34—34;

FIG. 35 is a view in perspective of the anvil;

FIG. 36 is a view in top plan of the actuator arm;

FIG. 37 is a view in elevation of the cartridge assembly of FIG. 33 looking into the back end.

FIG. 38 is a view in section similar to FIG. 33 showing the condition of the cartridge when a staple has just been picked up by the jaws and the anvil has started to move downwardly;

FIG. 39 is a longitudinally sectional view similar to FIG. 34 showing the condition illustrated in FIG. 38;

FIG. 40 is a view in section of FIG. 38 taken along line 40—40;

FIG. 41 is a section in view of FIG. 38 taken along line 41—41;

FIG. 42 is a section in view similar to FIG. 38 showing the condition of a cartridge shortly after a clip has been picked up by the jaws and the cartridge housing assembly has been slightly retracted;

FIG. 43a is a detail in top plan of the clip retainer spring;

FIG. 43b is a detail in side view of the clip retainer spring;

DETAILED DESCRIPTION OF THE PREFERRED EMBODIMENT

Figures 44, 45, 46:
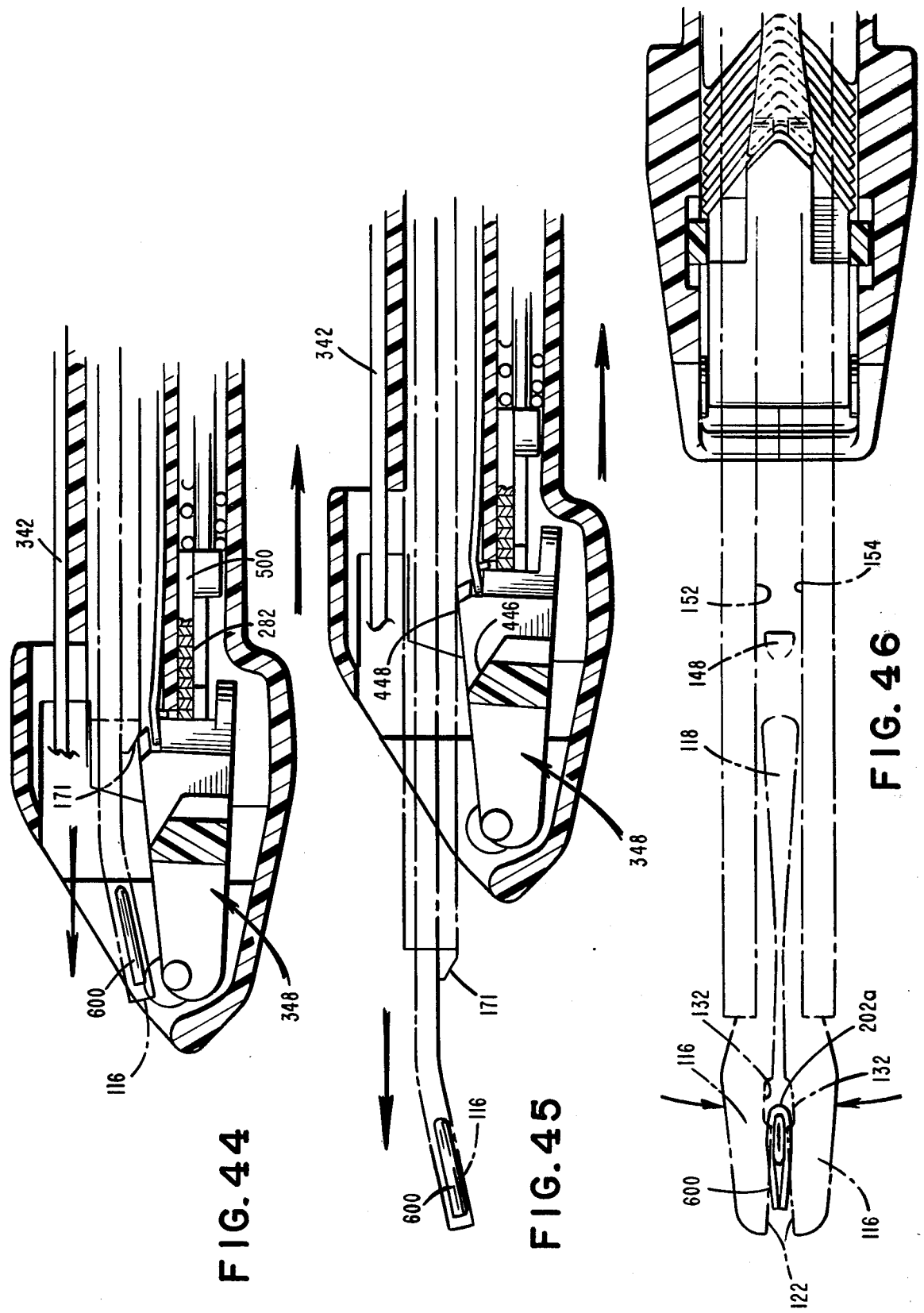
FIG. 44 is a view in section similar to FIG. 38 showing the cartridge housing assembly having been retracted to the point where the jaws are ready to emerge.
FIG. 45 is a sectional view similar to FIG. 38 showing the jaws fully emerged from the retracted cartridge housing assembly.
FIG. 46 is a sectional view similar to FIG. 39 illustrating the clinching of a clip.

Referring now to the drawings in detail, FIGS. 1-5 show the preferred embodiment of the inventive system for applying surgical clamps or clips which system is comprised of an instrument 10 and a detachably mounted disposable cartridge 12. The instrument 10 is illustrated in detail in FIGS. 9-17 and consists of a body or housing 20 of generally trapezoidal shape having a rearward projection 22 extending from its longer base. The housing 20 defines a central throughbore 24 which extends also through projection 22. An actuator rod 26 is slidably received in bore 24 and consists of a cylindrical piece bifurcated at one end 26a by slot 28 to form legs 28a and 28b each having a hole 30 defined near its free end and having a bevel 32 on its inner surface at its free end. The main portion of the cylindrical piece defines a throughbore 34 rectangular in cross section that extends from the bottom of slot 28 axially along the actuator rod 26. Near its other end 26b, the rod 26 is cut out on opposed sides to define flats 36 and 38 and at its other end 26b to define flats 40 and 42. The terminal part of the other end 26b is bevelled at 44 on opposite sides, 90° displaced from flats 40 and 42. A flange 46 separates flats 36 and 40 on one side, and flats 38 and 42 on the other side.

A pair of slots 50 is defined on each side toward the rear of the housing 20 and accommodate and receive the ends of a pair of ring handles 52, each comprised of a finger ring 54, a shank 56 and an actuating lever 58 joined at right angles to the shank 56. A hole 60 is defined at the junction 61 between the shank 56 and the actuating lever portion 58. The actuating lever 58 carries a boss 62 which projects from the edge of the lever 58 remote from the shank 56. The free end of the lever 58 is cut out at shoulder 59 and defines a slightly bulbous tongue 64 beveled at its terminal edge 66. Tongue 64 extends from one surface of the lever 58 with the cut out part being taken from the opposite surface. The hole 60 defined at the juncture 61 of the lever 58 and shank 56, receives a pivot pin 70 set into the housing 20, and in this fashion, each ring handle 52 is pivotally connected to the housing 20. When so pivotally connected, the tongue 64 of one ring handle 52 is received on flat 36 of the actuator rod 26 and the tongue 64 of the other ring handle 52 is received on flat 38, each bearing against a shoulder defined by the actuator rod between the respective flat 36 or 38 and the bifurcated end 26a of the rod 26. Because tongue 64 extends from one surface of the lever 58, the two ring handles 52 are complementary and interchangeable. When the ring handles 52 are pivotally mounted in the housing 20 by means of pivot pins 70, compresssion springs 72 are received at one end around the bosses 62, which serve as spring sockets, with their other ends bearing against an interior wall of the housing 20. Hence, upon actuation of the ring handles 52 by drawing them together, they will pivot about the pins 70 and the bell crank action of lever 58 will cause the actuator rod 26 to be advanced out of the throughbore 24 and the housing 20. The action is illustrated in FIGS. 2, 15 and 15a.

Projection 22, at the rear of the housing 20, is formed with an internal wall section 80 that defines a restriction 81 of the throughbore 24. Wall section 80 acts as a stop for the actuator rod 26. The end of projection 22 is closed by an end cap 82 which has an attached skirt that is received snuggly within projection 22. End cap 82 defines an opening 84 through which passes stud 86 of release plunger 90. A button 88 is formed on the exposed end of stud 86 and within the projection 22 an enlarged ring 92 is formed on stud 86 spaced a short distance from its inner end 94. The diameter or profile of end 94 is slightly less than that of the opening 81 provided in wall section 80, so that upon depressing the release plunger 90, the end 94 may project into the wall section 80, as illustrated in FIGS. 16 and 16a. The end 94 of the release plunger 90 is provided with a recess 96 having a flared entrance 98, see FIGS. 14 and 14a. A wear ring 100, having an opening 102 matching opening 81 and accommodating end 94 of release plunger 90, is received within the interior of the projection 22 in an abutting relationship with the wall section 80.

The quick detachable disposable cartridge is comprised of a jaw blade 110, shown in FIG. 8, a sleeve 112, shown in FIGS. 6, 6a and 7, and a cartridge housing assembly generally indicated by the reference numeral 114 and shown in FIGS. 1, 2, 3, 18, 19 and 20. The jaw blade 110 is fabricated with a pair of opposing jaws 116 at one end by means of slot 118 defining legs 117 and 119. The jaws 116 are bent out of the plane of the jaw blade 110 and indicated at 120 defining an angle of approximately 165°.

A pair of longitudinally extending flanges 122 project from the edges of each jaw 116.

The flanges 122 flare outwardly and the bottom of slot 126 defines a V-shaped groove 130,, in its center, see FIG. 20. The slot 126 extends from the tip of the jaw 116 rearwardly and opens into a transverse rectangularly shaped cutout 132, best shown in FIG. 19. The jaw blade 110 is also bifurcated at its other end by means of slot 134 to from legs 136 and 138. The end of each leg is provided with an inclined outer edge 140, which terminates at a recess 142. the legs 136 and 138 have resiliency and can flex towards each other from the reposed position shown in FIG. 8. Adjacent the other end of the jaw blade 110 are rectangularlyshaped slots 144 and 146, longitudinally displaced from one another. Toward the first end of the jaw blade 110, a tab 148 is punched and bent out of the plane of the jaw blade 110 to define an index actuator stop.

The sleeve or wrap 112 of the cartridge assembly is comprised of an elongated wrap that is formed from flat stock into a box 150 with the edges 152 and 154 left spaced apart to define a slot 156. A pair of ears 158 and 159 are formed on opposite sides of the box 150 near one end as shown in FIGS. 4, 5 and 6. Near its opposite end, the sleeve 112 is formed with a tab 160 that is pushed into the plane of slot 156. Tab 160 serves as a stroke stop. Also a projection 162 projects from sleeve 112 from the side opposite slot 156 and projection 162 serves as a cartridge stop. A rectangular cutout 164 with a cantilevered elongated spring detent 166 extending longitudinally from one end of cutout 164 is formed near the opposite end of sleeve 112. The free end 167 of the spring detent 166 lies spaced from the other end of cutout 164 and spring detent 166 is formed with a detent 170 that projects out of the plane of sleeve 112 in the same sense as projection 162. The free end 167 is bent into the plane of slot 144. A depending bevelled tab 171 is located on the bottom wall of box 150.

The jaw blade 110 and sleeve or wrap 112 are assembled together for relative sliding motion. When assembled, the jaw blade 110 fits within the box structure of the sleeve or wrap 112, as shown in FIGS. 4 and 5. The spring detent 166 of wrap 112 lies within the rectangular slot 144 of jaw blade 110 as best shown in FIGS. 14 and 15. Tab 160 is received within the rectangular cutout 146 and coacts therewith to establish a stroke stop by contacting the end 147 of slot 146 that is proximal to jaws 116. The legs 117 and 119 of the jaw blade 110 are formed with inclined edges or surfaces 172 and 174 which coact with the end 176 of wrap or sleeve 112. When sleeve 112 is advanced relative to jaw blade 110, by being moved in the direction of the jaws 116, the edge of end 176 engages the inclined surfaces 172 and 174 of jaw blade 110 forcing the jaws 116 to close together. This action is illustrated in FIG. 2.

The insertion of jaw blade 110, assembled with the wrap or sleeve 112, into the instrument is best illustrated in FIGS. 14, 15, 16 and 17. The jaw blade 110 is inserted into the instrument 10 by introducing legs 136 and 138 into the throughbore 34 at the bottom of slot 28 until they pass completely therethrough and project out from the other end, as shown in dotted lines. The incline surfaces 140 at the extreme ends of legs 136 and 138 contact wall section 80 and wear ring 100, are flexed inwardly to pass therethrough and blade 110 comes to rest with the wall section 80 and wear ring 100 received in the slots 142, thereby positively locking the jaw blade 110 into the instrument 10. When the extreme ends of the legs 136 and 138 are forced through the restrictions defined by the wall section 80 and wear ring 100, they are initially flexed or cammed inwardly by the inclined surfaces 140 and thereafter snap outwardly when the restrictions align with the grooves or slots 142. This action is best illustrated in FIG. 14. In this state, the tips of the inclined surface 140 at the ends of the legs 136 and 138 are received in the flared portion 98 of the recess 96 formed in the release plunger 90. During insertion, detent 170 is brought into engagement with and is received in one of the holes 30, depending upon the orientation of the jaw balde 110 and assembled wrap or sleeve 112. It will be noted, however, that regardless of the orientation, whether up or down, the detent 170 will be received in one of the holes 30. Therefore, it is not necessary for a surgeon inserting the jaw blade 110 into the instrument to take special precautions to be sure that the jaw blade 110 is in particular orientation with respect to the instrument; he or shee may freely insert the jaw blade 110 in either of the two possible orientations.

With the detent 170 received in a hole 30 as illustrated in FIG. 14a, the instrument is actuated by closing the handles 52 together in the manner demonstrated in FIG. 2. The closing of the handles causes the levers 58, due to the bell crank action, to advance the actuator rod 26 out of the instrument in the direction of the arrow 180 in FIG. 15. It will be noted that the jaw blade 110 is stationary relative to the instrument and the advancement of the actuator rod 26 only carries with it the wrap or sleeve 112. Tab 160 coacts with end 147 of slot 146 of the jaw blade 110 to serve as a stroke stop and allow the sleeve 112 to slide relative to the jaw blade 110 only a predetermined amount. During advancement, the forward edge of the sleeve 112 contacts the inclined surfaces 172 and 174 of legs 117 and 119 to cam jaws 116 to a closed position as illustrated in FIG. 2. The condition of the apparatus at this time is as illustrated in FIGS. 15 and 15a.

It is, of course, understood that a cartridge housing assembly 114 is slidably mounted or carried on the jaw blade 110 and assembled sleeve 112. The action of the cartridge housing assembly 114 and its structure will be described in detail hereinafter, but for purposes of the description at this point, it may be assumed that the cartridge housing assembly 114 is simply carried on the jaw blade 110 and 112 and is free to slide from a position where it contacts projection 162 on sleeve 112 and to where it contacts ears 158 and 159 on sleeve 112.

When a disposable cartridge has been fully used or consumed, it is ejected from the instrument by the following action. The ejection plunger 90 is depressed or pushed inwardly toward the projection 22. This causes the flared portion 98 of recess 96 to ride up the inclined surfaces 140 at the end of legs 136 and 138 of the jaw blade 110 and to cam the legs together and release slots 142 from engagement with the restricted openings defined by the wall section 80 and wear ring 100. The cartridge may then be simply withdrawn from the throughbore 34 and discarded.

The sliding motion of the sleeve 112 relative to the jaw blade 110 in the opposite sense is motivated by the springs 72 and resiliency of legs 117 and 119 and is controlled by the fact that the free end 167 of the spring detent 166 is bent up into the plane of the jaw blade 110 and is received within the rectangular slot 144. End 145 of the slot 144 coacts with the free end 167 of the spring detent 166 to stop further relative sliding motion between the jaw blade 110 and the sleeve 112 in this sense.

A novel clip or clamp as used in the present invention is illustrated in FIGS. 21 and 22 and consists of a small wire 200 rectangular in cross section with rounded corners bent into a substantial V-shape having an apex bend 202, straight extending inner legs 204 and outer legs 206, which are integrally formed with legs 204. A slight bend 208 defines an angle between the legs sections 204 and 206 of from about 160° to about 175°. The inner surface 210 of the clip 200 is provided with a plurality of V-shaped grooves 212 which are cut or pressed transversely of the surface 210. A clinched clip or clamp is shown in FIG. 23 and it will be noted that when clinched, a space 214 is defined between the leg portions 204 and 206 which space tapers gradually, terminating at the point that the two ends 216 of the clip are contacted. The apex bend 202 is transformed during clinching into a U bend 202a. The bends 208 act to assist in the formation of the defined space 214. The geometry of this space is specially designed and arranged to accommodate, in the best mode possible, those hollow vessels which are required to be clamped off by the apparatus of the present invention. The clip is made of a malleable inert surgical inplant material such as 316 stainless steel or tanlalum. The actual shape of the closed clip will vary according to the amount of tissue enclosed by the clip. When the amount of tissue is small, the legs 204 and 206 become parallel and almost touching.

The remainder of the cartridge assembly will now be described. As already noted, a cartridge housing assembly 114 is received on the jaw blade 110 and sleeve or wrap 112 assembly and is slidably arranged relative thereto. The assembly 114 contains a stack of clips or clamps and is arranged to coact with the jaw blade 110 and jaws 116, when properly manipulated, to present its stack of clips one at a time to the jaws 116. The cartridge housing is shown in detail in FIGS. 24 through 29 and is comprised of a boxlike structure formed from a pair of complementary body halves 260, one of which is shown in FIGS. 28 and 29. Each body half 260 is made of suitable plastic material or the like and is elongated in configuration having a nose portion 262 at one end, the exterior of which is rounded as appears in FIGS. 25 and 26. The portion of the body half 260 from the nose portion 262 to its other end is generally right angled in configuration so that the two body halves 260 when placed together create a box-like structure comprised of a top wall structure (to be described hereinafter), side walls 270 and a bottom wall structure composed of sloping walls 278 which join at a lower apex line 279. A generally rectangular inner space 264 is defined in the upper portion of the housing above longitudinally extending ribs 266. Within the box-like structure, ribs 268 define in combination with the ribs 266 and bottom walls 278 an interior space 280 geometrically designed to receive a stack of clips 282 as shown in FIG. 33. The edges of the ribs 268 are spaced apart, whereas the edges of the ribs 266 abut. One of the body halves 260 is formed with projections 284, 286 and 288 and the other body half 260 is formed with mating recesses, the projections and recesses coacting for alignment of the two body halves 260 during the fabrication of the cartridge housing. Each body half 260 further is provided with a longitudinally extending recess 290 formed in the interior of side wall 270 which defines a shoulder 292 at the end of the recess or slot 290 distal to the nose portion 262. A further right angled recess or slot 294 is defined in the nose portion 262 which extends vertically from floor to roof of the nose portion 262 and thence longitudinally to the rear. Recess 296 is molded into the forward part of nose portion 262 and is surrounded by a reinforced ring 298. The forward part of nose portion 262 is open as shown. The ribs 266 terminate at their ends proximal to the nose portion 262 at an angle to the transverse plane of the body housing so that the pair of ribs 266 defines a V as illustrated in FIG. 24 and as referenced by the numeral 300 to allow clips to pass. Ribs 268 also terminate in the nose portion 262 at an angle 301 but have rectangular portions 303 adjacent the side walls. Reinforcing ribs 302, 304 and 306 extend transversely spaced longitudinally and coact to guide the sleeve or wrap 112. The ribs 302 and 304 are profiled at the top of their abutting ends to a V-shape as indicated by the reference numeral 308 and ribs 302 are cut out at the bottom of their abutting ends to define an opening 310. Also, the ribs 302 are cut out, as indicated by the reference numeral 312, to reduce their longitudinal extension in the plane of cutout 310. The ribs 304 are also cut out at their lower ends to reduce their longitudinal extensions and to establish a recess 314. The bottom wall 278 of body half 260 is cut out as indicated by reference numeral 316. Abutting cutout 316 is a rib 318 which extends normal to rib 268. Top wall 274 extends from nose portions 262 rearwardly and defines cutout or slot 275. Above the top wall 274 and parallel to it is a wall 320 which extends longitudinally from just forward of rib 304 to about halfway between ribs 304 and 306. At the end of wall 320, distal from the nose portion 262 is a tab 322 that is above the wall section 320 and extends transversely of the cartridge housing. Tabs 322 abut but walls 320 are spaced apart. The end of body half 260 opposite the nose portion 262 is provided with an upstanding flange 324 which defines a step 326. The rear of top wall 274 and side walls 270 are connected to rounded terminal portion 330 by a transition 328.

When the two body halves 260 are assembled, the top walls 274 abut at each end of the body housing, the tabs 322 abut and the upper walls and lower walls of the nose portion 262 abut, leaving a front opening 263.

the parts incorporated within the body housing of the assembly 114 include a compression spring 340, an actuator arm 342, a clip pusher 344, a spring 346 for the clip pusher, an anvil 348, a retainer spring 350 and a socket plate 352.

The anvil 348 is illustrated in FIG. 35 and is comprised of a block-like member thinner at its forward end to define an upper inclined surface 440, a pair of pivot projections 442 on either side of the thin end, a V-shaped shoulder 444 defined at its rear narrowed end 448, a pair of side ramps 446 which flank the reduced rear section 448 and a lower rear tab 450. The shoulder 444 is limited by a vertical V wall 445 which joins an inclined V wall 447 leading to the edge of top surface 440. In addition, a pair of vertical side plates 452 are attached on opposite sides of the anvil 348 adjacent the ramps 446. The anvil is inserted into the cartridge housing with the pivot projections 442 received in the recess 296 and side plates 452 received in recesses 294.

The actuator arm 342 is a plate in the shape of a T with the ends of the cross bar 364 cutout at 366 to fit and coact with the upper ends of the plates 452 of anvil 348 in the manner illustrated in FIG. 36 and shown in FIG. 33. A tab 368 depends from the free end of the main bar of the actuator arm 342. The actuator arm 342 is positioned in the body housing with the ends of the cross bar received in recesses 294, the cutouts 366 receiving the upper ends of plates 452, and the main bar of the actuator arm overlying top wall 274 and underlying wall section 320. Depending tab 368 extends vertically into space 264 and aligns with index tab 148 of jaw blade 110. Tab 368 is biased by spring 340 which also bears on the rear end of slot 275. Tabs 322 hold spring 340 in place.

The retaining spring 350 is shown in FIGS. 43a and 43b and is comprised of a profiled leaf spring having a pair of slots 480 spaced from wide end 482. Beyond slots 480, the width is reduced at 484 to point 485, beyond which spring 350 flares at edges 486 terminating in a V-edge or end forming ears 488 which end is bent downwardly along line 490. A tab 492 depends downwardly at the bend line 490 normal to the plane of end 488. Spring 350 is inserted into the box-like housing with end 482 received in recess 314, slots 480 coacting with ribs 302, recess 312 and cutout 310 to hold down spring 350, and the V-shaped end (ears 488) engaging surfaces 447 and 445 to overlie a clip 600 on shoulder 444. Tab 492 just clears shoulder 444 and also acts to hold the clip thereon, see FIG. 33.

The clips are stacked one behind the other in tight order and ride on ribs 268. Clip pusher 344 is illustrated in FIGS. 33, 38, 40 and 41 and is comprised of a plate 500 presenting a V-edge 502 complementary to a clip 600, a boss 504 formed on the lower rear edge of the plate 500 and a rod 506 extending from boss 504. Clip pusher 344 fits into space 280 of the housing with plate 500 riding on ribs 268, boss 504 fitting into the space between ribs 268 and rod 506 extending between ribs 268 and guiding biasing spring 346. The other end of spring 346 bears against a socket plate 352 that is inserted into the housing in cutouts 316 and is held by ribs 318.

the cartridge housing assembly coacts with the jaw blade 110 and wrap 112 assembly as follows. The blade 110 and wrap 112 assembly pass through space 264 of the cartridge housing assembly 114 which is constrained thereon in one sense by projection 162 on wrap 112 and in the other sense by ears 158 and 159 on wrap 112 and shoulder 292 in recess 290.

The original condition of the disposable cartridge is illustrated in FIG. 30. In the several views showing the interrelationship of the cartridge housing assembly 114 and the jaw blade 110 and wrap 112 assembly, the jaw bladewrap assembly is shown in phantom. In FIG. 30, the cartridge housing assembly is retracted toward the instrument 10 in relation to the jaw blade-wrap assembly and thus, the jaws 116 are projected out from the nose portion with the wrap 112 contacting the upper rear edge of the inclined surface 440 and the narrowed rear section 448. Thus, the anvil 348 is pivoted slightly downwardly but no clip is located on shoulder 444.

When the disposable cartridge is brought to the staple loading position, the cartridge housing assembly 114 is advanced along the jaw blade-wrap assembly until the jaws 116 are brought within the nose portion to the position as illustrated in FIGS. 33 and 34. At this time, however, there is no clip 600 resting on shoulder 444. Otherwise, the relationship of the parts is as shown in FIGS. 33 and 34 and tab 148 on jaw blade 110 is contacted against depending tab 368 of the actuation arm 342.

To load a clip on shoulder 444, the cartridge housing assembly 114 is advanced slightly over the jaw blade-wrap assembly and this causes the anvil 348 to be pivoted downwardly to the position illustrated in FIG. 32 whereat the shoulder 444 aligns with the clip stack and receives the leading clip due to the bias afforded by the clip pusher spring 346. The downward pivot of the anvil 348 is caused by tab 148 preventing actuation arm 342 from following the advancement of the cartridge housing assembly during this slight further advancing movement. Upon release or relief of the cartridge housing assembly, spring 340, which has been biased during the downward pivot of 348, will return or restore the cartridge housing assembly to its relative position with respect to jaws 116 as illustrated in FIGS. 33 and 34. At this time, however, a clip 600 is sitting on shoulder 444 with the clip legs 204 and 206 angled slightly downwardly due to the profile of shoulder 444. This position of clip 600 aligns with the downward angle of jaws 116 and the clip is ready to be picked up by the jaws 116 whenever the cartridge housing assembly is next retracted. Also, clip spring retainer 350 will overlie the clip 600 holding it on shoulder 444.

The pick up of a clip 600 occurs by further retracting the cartridge housing assembly along the jaw blade-wrap assembly. During pick-up, the clip 600 is compressed somewhat into an open U-shape form from its original V-shape as illustrated in FIG. 39. A comparison of FIGS. 39 and 41 will show the extent of working of the clip 600 by jaws 116 and anvil portion 448. As the clip 600 is being picked up by the jaws 116, the legs of the clip are received in slots 126 and immediately thereafter, the ends of jaws 116 strike ramps 446 pivoting anvil 348 downwardly and forcing actuator arm 342 to compress spring 340 through the bellcrank levering of side plates 452. This action lowers the anvil 348 away from the now entrapped clip so that the clip can clear the end of narrowed section 448 and be taken away from the influence of the retaining spring 350. This action is illustrated in FIGS. 38 and 39 from which one sees that the anvil 348 has been lowered by the jaws 116. This action, of course, takes place during retraction of the cartridge housing assembly.

Continued retraction of the cartridge housing assembly produces the condition as shown in FIG. 42. The jaws 116 are now contacting the upper inclined surface 440 to hold the anvil 348 down out of the way as the cartridge housing assembly is being further retracted. Eventually, the jaws 116 begin to clear through the opening 263 in the nose portion, and, at this time, the bevel 171 formed on the underside of wrap 112 contacts the rear edge of the narrowed end 448 to move anvil 348 down while the jaw 116 clear through the opening 263 and emerge totally from the cartridge housing assembly. The jaws 116 are open, but holding a clip ready to be clinched. The cleared jaws 116 are shown in FIG. 45 and the clinching action already described is shown in FIG. 46. For maximum visibility and access to the surgical field the cartridge housing 114 is moved to its retracted most position adjacent to instrument 10. Following clinching, the disposable cartridge is once again in the condition as shown in FIG. 30. The procedure is repeated as long as clips remain in magazine.

A barrel sleeve 700 having an axially extending lens 702 is shown in FIG. 1a. Barrel sleeve 700 fits around and is freely rotatably mounted on the cartridge housing and bears at its forward end against nose portion 262 and at its rear end on step 326 flange 324. The end portion 330 of the cartridge housing is rounded to accommodate the barrel sleeve 700. Thus, when handling the cartridge housing assembly 114, a surgeon will not impose any torsion or torque due to twisting. The barrel is also provided with ridges 704 to improve gripping. Lens 702 allows one to see into the magazine and monitor the clip stack.

Although the present invention has been shown and described in terms of a specific preferred embodiment, it will be appreciated by one skilled in the art that changes and modifications are possible which do not depart from the inventive concepts described and taught herein. Such changes and modifications are deemed to fall within the purview of these inventive concepts.

What is claimed is:

1. A novel system for applying surgical clips comprising an instrument and a disposable cartridge,
   (1) said disposable cartridge having
      (a) elongated blade means defining at one end a pair of opposed jaws resiliently spaced apart,
      (b) actuation means movable relative to said blade means to close said jaws together, and
      (c) cartridge housing means movably mounted on said blade means adapted to contain a plurality of surgical clips and feed them singly to a predetermined position relative to the jaws of said blade means so that movement of cartridge housing means relative to said blade means will transfer the clip in said predetermined position to said jaws properly oriented to be clinched by said jaws,
   (2) said instrument comprising
      (d) a body, and
      (e) driver means mounted on said body for movement, said instrument and disposable cartridge defining mutually coacting quick detachable means to quick detachably fix said disposable cartridge in said instrument with said actuation means drivable by said driver means to close the jaws of said blade means to clinch a clip held therein.

2. A novel system according to claim 1 wherein said actuation means is in the form of a wrap surrounding said blade means and slidably arranged relative thereto.

3. A novel system according to claim 1 wherein said mutually coacting quick detachable means includes detent means and detent receiving means.

4. A novel system according to claim 1 wherein said instrument further includes ring handles pivotally mounted on said body to operate said driver means.

5. A novel system according to claim 1 wherein said driver means is in the form of a shaft slidably received in a bore defined in said instrument body.

6. A novel system according to claim 1 wherein said cartridge housing means includes a clip magazine means having a biased clip pusher and anvil means pivotally mounted in said cartridge housing means for receiving a clip in a first pivoted position and pivoting to said predetermined position.

7. A novel system according to claim 6 wherein said cartridge housing means includes lever means for pivoting said anvil means.

8. A novel system for applying surgical clips comprising an instrument and a disposable cartridge,
   (1) said cartridge comprising:
      (a) elongated blade means defining at one end a pair of opposed jaws resiliently spaced apart and at its other end a first component of a first quick detachable means,
      (b) actuation means movable relative to said blade means to close said jaws together and including a first component of a second quick detachable means, and
      (c) cartridge housing means movably mounted on said blade means adapted to contain a plurality of surgical clips and feed them singly to a predetermined position relative to the jaws of said blade means so that movement of cartridge housing means relative to said blade means will transfer the clip in said predetermined position to said jaws properly oriented to be clinched by said jaws, and
   (2) said instrument comprising
      (d) a body,
      (e) a driver means mounted for movement in said body,
      (f) movable handle means mounted in said body,
      (g) means for translating motion of said handle means into movement of said driver means,
      (h) a second component of said first quick detachable means mounted on said body for cooperation with said first component of said first quick detachable means to fix quick detachably said elongated blade means on said body, and
      (i) a second component of said second quick detachable means cooperating with said first component of said second quick detachable means to fix quick detachably said actuation means on said driver member.

9. A novel system according to claim 8 wherein said actuation means is in the form of a wrap surrounding blade means and slidably arranged relative thereto.

10. A novel system according to claim 8 wherein said first and second quick detachable means include detent means and detent receiving means.

11. A novel system according to claim 8 wherein said handle means includes ring handles pivotally mounted on said body to operate said driver means.

12. A novel system according to claim 8 wherein said driver means is in the form of a shaft slidably received in a bore defined in said instrument body.

13. A novel system according to claim 8 wherein said cartridge housing means includes clip magazine means having a biased clip pusher and anvil means pivotally mounted in said cartridge housing means for receiving a clip in a first pivoted position and pivoting to said predetermined position.

14. A novel system according to claim 13 wherein said cartridge housing means includes lever means for pivoting said anvil means.

15. A disposable cartridge for use in a novel system for applying surgical clips including an instrument and a disposable cartridge quick detachably connected thereto, said cartridge comprising
   (a) elongated blade means defining at one end a pair of opposed jaws resiliently spaced apart and at is other end a first component of a first quick detachable means
   (b) acutation means movable relative to said blade to close said jaws together and including a first component of a second quick detachable means
   (c) cartridge housing means movably mounted on said blade means adapted to contain a plurality of surgical clips and feed them singly to a predetermined position relative to the jaws of said blade means so that movement of cartridge housing means relative to said blade means will transfer the clip in said predetermined position to said jaws properly oriented to be clinched by said jaws, said cartridge adapted to be quick detachably connected to an instrument provided with complementary components of said quick detachable means.

16. A disposable cartridge according to claim 15 wherein said actuation means is in the form of a wrap surrounding said blade means and slidably arranged relative thereto.

17. A disposable cartridge according to claim 15 wherein said first and second detachable means includes detent means.

18. A disposable cartridge according to claim 15 wherein said cartridge housing means includes clip magazine means having a biased clip pusher and anvil means pivotally mounted in said cartridge housing means and receiving a clip in a first pivoted position and pivoting to said predetermined position.

19. A novel system according to claim 18 wherein said cartridge housing means includes lever means for pivoting said anvil means.

20. An instrument for use in a novel system for applying surgical clips including the instrument and a disposable cartridge quick detachably connected thereto, said instrument comprising:
  (a) a body containing a component of first quick detachable means,
  (b) a driver member mounted in said body for reciprocal movement between an inoperative and an operative position and containing a component of said quick detachable means, complementary components of said first and said second quick detachable means being included in a disposable cartridge adapted to be connected to the instrument,
  (c) actuating means attached to said body and operable to reciprocate said driver member, and
  (d) bias means for biasing said actuating means into a first position in which said driver member is moved to its inoperative position.

21. A novel system for applying surgical clips comprising a disposable cartridge connected to an instrument,
(1) said disposable cartridge having
  (a) elongated blade means for forming a blade having one end bifurcated to form jaw means for holding a surgical clip and the other end bifurcated to form one component of first connections means,
  (b) actuating means longitudinally movable relative to said blade means for closing said jaw means and having one component of second connection means,
  (c) cartridge housing means for holding a plurality of surgical clips and being mounted for longitudinal movement relative to said blade means, said cartridge housing means being reciprocal with respect to said blade means to transfer surgical clips successively to said jaw means, said cartridge housing means including means cooperating with said jaw means for partially compressing clips being transferred from said cartridge housing means to said jaw means, and
(2) said instrument having
  (d) a body having another component of the first connection means, said first connection means providing means for connecting said blade means to said body,
  (e) driver means connected to said body for moving said actuation means towards and away from said body, said driver means having another component of the second connection means, said second connection means providing means for connecting said actuation means to said driver means, and
  (f) driving means connected to said body for actuating said driver means to move said actuation means thereby compressing a surgical clip held by said jaw means.

22. A novel system according to claim 21 further comprising movement limiting means for limiting movement of said actuation means towards said body, a first component of said movement limiting means being associated with said actuation means and a second component of said movement limiting means being associated with said blade means, said components being engageable with each other to limit movement of said actuation means towards said body.

23. A novel system according to claim 21 wherein said body includes ejector means for separating said components of said first connection means thereby facilitating removal of said blade means from said body.

24. A novel system according to claim 21 wherein said disposable cartridge further includes barrel means reciprocal with said cartridge housing means and independently rotatable about said cartridge housing means, said barrel means providing means for holding and for moving said disposable cartridge with respect to said blade means.

25. A novel system according to claim 21 wherein said jaw means are positioned at an angle with respect to said actuation means.

26. A novel system for applying surgical clips comprising an instrument, a disposable cartridge and connecting means for releasably connecting the cartridge to the instrument,
(1) the instrument including:
  (a) a body,
  (b) trigger means pivotally connected to said body, and
  (c) movement means carried by said body and operatively associated with said trigger means for movement along an axis, said trigger means providing means for moving said movement means along the axis;
(2) the disposable cartridge including:
  (d) an elongate strip having an enlarged end bifurcated to form jaw members,
  (e) an elongated wrap at least partially surrounding said strip and longitudinally movable along the axis of said movement means, one end of said wrap being adapted to contact the enlarged end of the elongate strip and compress said jaw members during movement of said wrap, and
  (f) cartridge means for containing a plurality of surgical clips and being mounted for reciprocal longitudinal movement with respect to said elongate strip, reciprocal movement of said cartridge means sequentially transferring surgical clips from said cartridge means to a predetermined position in said jaw members; and
(3) the connecting means including:
  (g) first connection means having one component associated with said body and one component associated with said elongate strip, said components being engageable with each other to connect said elongate strip to said body,
  (h) second connection means having one component associated with said movement means and one component associated with said elongate wrap, said components being engageable with each other in such manner that said elongate wrap is connected to said movement means and is moved by the movement of said movement means along said axis so that said one end of said wrap contacts and compresses said jaw members.

27. A system for feeding surgical clips comprising:
(a) elongated blade means defining at one end a pair of opposed jaws spaced apart; and
(b) cartridge housing means movably mounted on said blade means adapted to contain a plurality of surgical clips and to feed them singly and successively to a predetermined position relative to said jaws of said blade means so that movement of said cartridge housing means relative to said blade means will transfer the one clip in said predetermined position to said jaws.

* * * * *